US008656754B2

(12) United States Patent
Kawana

(10) Patent No.: US 8,656,754 B2
(45) Date of Patent: Feb. 25, 2014

(54) GAS CHROMATOGRAPH APPARATUS

(75) Inventor: Shuichi Kawana, Osaka (JP)

(73) Assignee: Shimadzu Corporation, Kyoto-Shi (JP)

( * ) Notice: Subject to any disclaimer, the term of this patent is extended or adjusted under 35 U.S.C. 154(b) by 645 days.

(21) Appl. No.: 12/909,724

(22) Filed: Oct. 21, 2010

(65) Prior Publication Data
US 2011/0100093 A1 May 5, 2011

(30) Foreign Application Priority Data

Oct. 29, 2009 (JP) .................. 2009-248540

(51) Int. Cl.
G01N 30/32 (2006.01)
G01N 30/12 (2006.01)
G01N 30/54 (2006.01)
G01N 30/86 (2006.01)

(52) U.S. Cl.
USPC ....................... 73/23.42; 73/23.36

(58) Field of Classification Search
USPC ............... 73/23.35, 23.36, 23.41, 23.42; 96/101–103
See application file for complete search history.

(56) References Cited

U.S. PATENT DOCUMENTS

| 5,339,673 | A | | 8/1994 | Nakagawa et al. | ......... 73/23.36 |
| 5,467,635 | A | | 11/1995 | Nakagawa et al. | ......... 73/23.35 |
| 5,897,781 | A | * | 4/1999 | Dourdeville | ............... 210/656 |
| 5,938,817 | A | | 8/1999 | Shibamoto et al. | ............... 95/23 |

FOREIGN PATENT DOCUMENTS

| JP | 04-269655 | 9/1992 |
| JP | 2000-304751 | 11/2000 |
| JP | 2006-162515 | 6/2006 |

OTHER PUBLICATIONS

Extended European Search report for counterpart European Application No. 10188783.4, Dec. 14, 2010.

* cited by examiner

Primary Examiner — Daniel S Larkin
(74) Attorney, Agent, or Firm — Bingham McCutchen LLP

(57) ABSTRACT

The present invention aims at realizing an energy-saving mode in which the usage of a carrier gas and the power consumption are sufficiently suppressed without causing damage to the apparatus. When a command for executing the energy-saving mode is entered (S1), the column flow rate after the transition to the energy-saving mode (when the temperature decreases) is computed by using control parameters determined in correspondence to the energy-saving mode. If the flow rate exceeds the allowable upper limit determined by the configuration of the apparatus (S3 and S4), a warning for urging users to decrease the column inlet pressure and enter the command again is displayed (S11). If the computed flow rate is not higher than the allowable upper limit, a constant pressure control is performed aiming at the inlet pressure at that point in time (S5 and S6). Although the column flow rate gradually increases after the heater of the column oven is turned off, it will not exceed the allowable upper limit. Thus, the detector is prevented from being damaged.

8 Claims, 3 Drawing Sheets

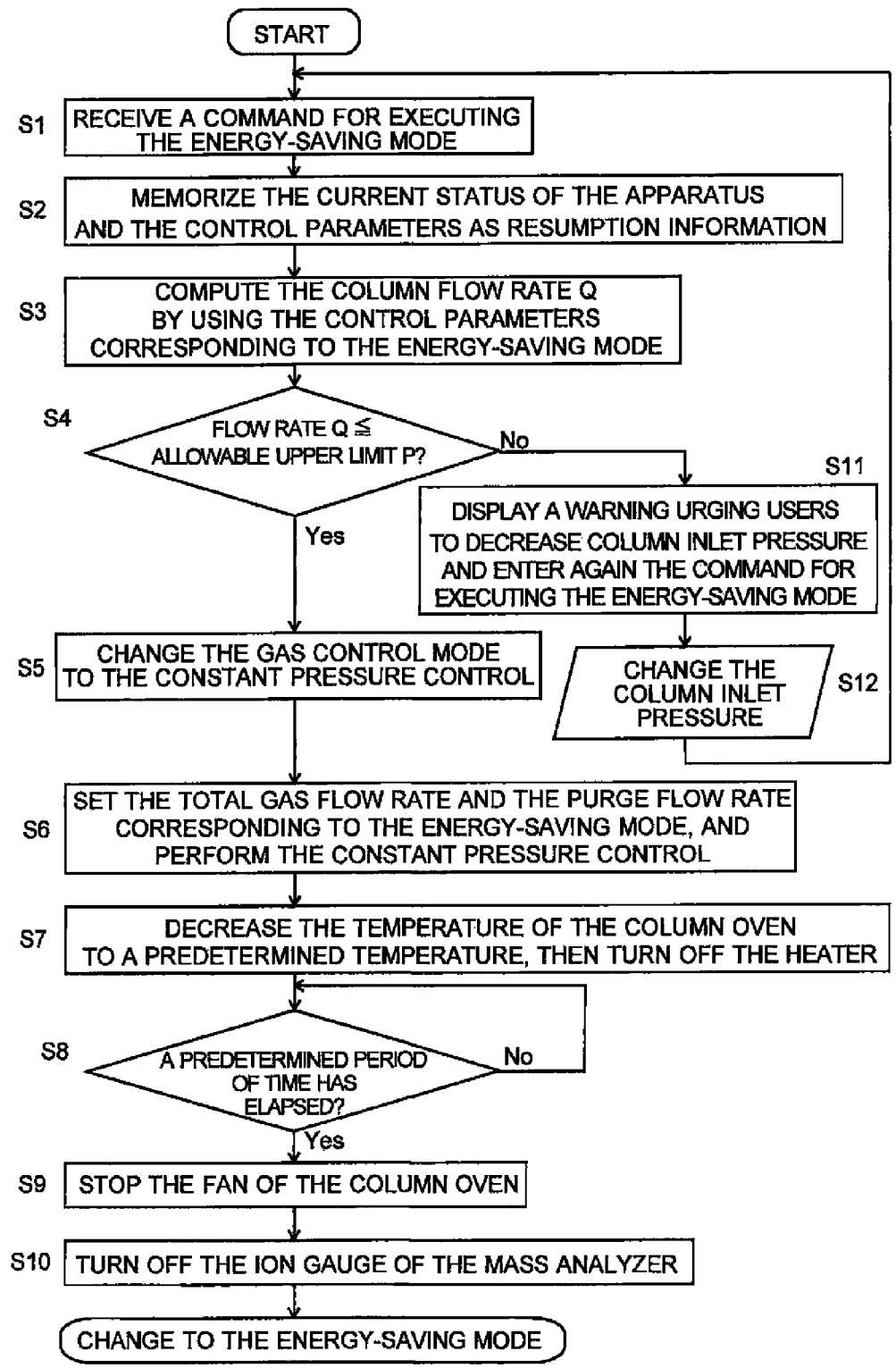

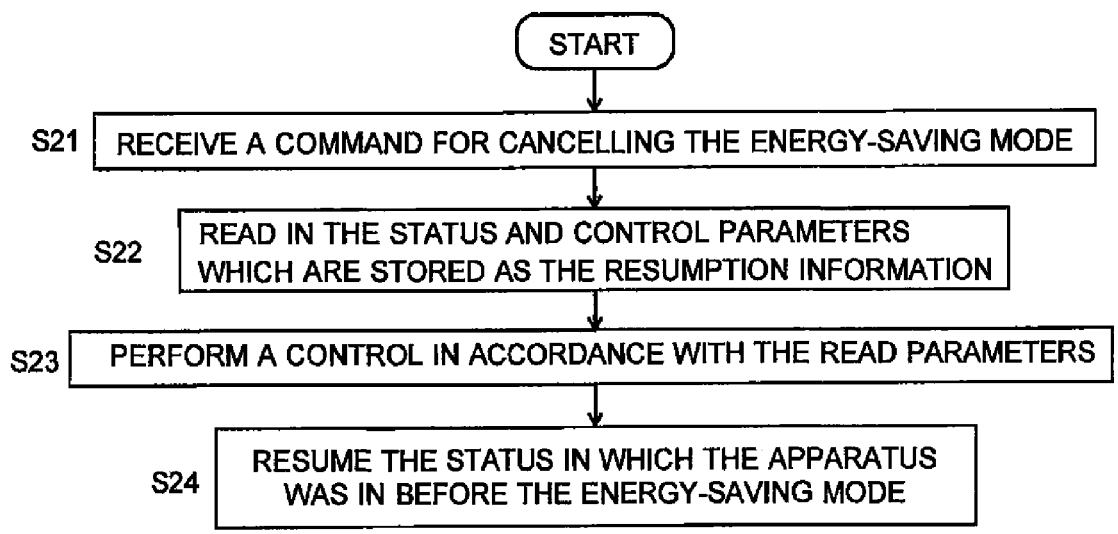

GAS CHROMATOGRAPH APPARATUS

The present invention relates to a gas chromatograph apparatus. More specifically, it relates to a control technique of a gas chromatograph apparatus. Since the gas chromatograph according to the present invention may have any kind of detector, the present invention also includes a gas chromatograph mass spectrometer in addition to a general gas chromatograph apparatus.

BACKGROUND OF THE INVENTION

In a gas chromatograph mass spectrometer (GC/MS), components in a sample are temporally separated in a column of a gas chromatograph (GC), and the separated components are sequentially injected into and detected by a mass spectrometer. Since a GC/MS requires a fairly long time to achieve a stable status in which an analyses can be performed from the moment when the power of the apparatus is activated, the power of the apparatus is seldom shut down and the power is generally kept on even if there is a time interval between the end of one analysis and the initiation of the next analysis. However, in actually performing an analysis, it is not uncommon that the time interval between the end of an analysis of one sample and the initiation of an analysis of the next sample is as long as from a few hours to more than a dozen hours. Therefore, there has been a demand for reducing the running cost required for the waiting period until the next analysis as much as possible both from the standpoint of environmental protection and the standpoint of cost reduction in a company or organization.

In the case of a GC/MS, wasteful consumption during the waiting period as previously described is mainly composed of the consumption of a gas (or a carrier gas) which is continuously supplied through the column of the GC and the consumption of the power for warming the column oven and other units and for driving a vacuum pump for evacuating a vacuum chamber. In a GC/MS, if the supply of a carrier gas is completely stopped during the waiting period, the inside of the column, which is connected to a mass spectrometer in a vacuum state, will be evacuated to a substantial vacuum level. This might deteriorate the column, e.g. the liquid phase applied to the inner wall of the column is damaged. Therefore, it is required to keep the carrier gas flowing at a low flow rate also during the waiting period, without stopping the supply of the carrier gas. In addition, a complete halt in heating the column oven during the waiting period causes the problem that it takes time to heat the inner wall of the oven, which has a large heat capacity, and other portion to perform the next analysis. Given these factors, in the GC described in Japanese Unexamined Patent Application Publication No. 2000-304751 for example, a user presets the temperature of a column oven to be approximately as low as the room temperature and presets the flow rate of a gas to be low for the waiting period, and when a daily shutdown (or a waiting mode) is activated, each unit is controlled so that the column oven temperature and the gas flow rate will be at the preset values.

However, conventional GCs have the following problem: with the aim of dealing with a variety of analyses, recent GCs provide a plurality of gas control modes for supplying a carrier gas to a column, such as a constant linear velocity control mode, a constant column flow rate control mode, and a constant pressure control mode. However, in some gas control modes, a decrease in the temperature of a column which extremely decreases the viscosity of the carrier gas may preclude an appropriate control, because, in an actual analysis, it is assumed that the column temperature will not be as low as room temperature for example. In the constant linear velocity control mode for example, the column inlet pressure is controlled so that the linear velocity of the gas flowing in the column is constant. If the viscosity of the carrier gas is extremely decreased, it is required to extremely decrease the column inlet pressure in order to maintain the linear velocity constant, which is beyond the controllable limits.

Particularly in the case of a GC/MS, there is an allowable upper limit of the gas flow rate injectable into a mass spectrometer. If the gas supply control is not appropriately performed as previously described, in some parameter settings, a gas may flow into the mass spectrometer with a flow rate beyond the allowable upper limit, which might cause damage to the mass spectrometer or some other problems.

In addition, in conventional GCs, the temperature of the column oven is maintained at the setting value even in the waiting mode, and the power is basically supplied to the heater which is provided for the column oven. However, in recent years, taking an action for reducing $CO_2$ emission and reducing cost have been further required. To this end, it is indispensable to shut down the power to the heater during the waiting mode. However, if the control is merely stopped to cease the power supply in a column oven having both a heater and an air fan, the temperature in the column oven may in some cases become too high due to the afterheat of the heater and damage the column.

SUMMARY OF THE INVENTION

The present invention has been developed in view of the aforementioned problem and the main objective thereof is to provide a gas chromatograph apparatus capable of reducing the usage of a carrier gas and the power consumption during a waiting period from the end of one analysis to the initiation of the next analysis without causing damage to the apparatus.

To solve the previously described problem, the present invention provides a gas chromatograph apparatus having at least two switchable operation modes, one mode being an analysis mode in which an analysis of a sample can be performed and the other mode being a waiting mode in which no analysis is performed, where the gas chromatograph apparatus includes: a column placed in a column oven; a sample vaporization chamber provided at an inlet of the column; a carrier gas passage for feeding a carrier gas to the sample vaporization chamber; a purge passage for ejecting an impurity gas from the sample vaporization chamber; a split passage for ejecting a portion of the carrier gas from the sample vaporization chamber; a flow controller for interlockingly controlling the flow rates of the gases flowing through the carrier gas passage, the purge gas passage and the split passage as well as the gas pressure in the sample vaporization chamber, the flow controller having a constant linear velocity control mode, a constant column flow rate control mode, and a constant pressure control mode, as a gas control mode; and a detector for detecting a sample component in a gas which has passed through the column, wherein the gas chromatograph apparatus further includes:

a) a memory for memorizing control parameters for the waiting mode, the control parameters including a minimum value of a gas flow rate required for each of the carrier gas passage and the purge passage in the waiting mode; and b) a controller for setting in a transition from the analysis mode to the waiting mode, the gas control mode to the constant pressure control mode regardless of the gas control mode in the analysis mode, for setting a column inlet pressure at that point in time as a target pressure, and for controlling the flow controller using the control parameters memorized in the memory, and the controller includes:

a flow rate determiner for estimating, in advance of the transition to the waiting mode, a column flow rate corresponding to a lowest predicted value of a temperature in the column after the transition to the waiting mode by using the control parameters memorized in the memory, and for comparing the estimated value with a preset threshold value; and a pressure changer for providing a warning to a user that the column inlet pressure at that point in time should be decreased or automatically decreasing the column inlet pressure in a case where the estimated value of the flow rate exceeds the threshold value.

The "waiting mode" can be referred to as an "energy-saving mode" or an "eco-mode" in that both the power consumption and the consumption of the carrier gas can be suppressed while the power supply to the apparatus itself is continued.

The control parameters which are memorized in the memory include a split ratio and/or other values in addition to the gas flow rate for the carrier gas passage (or the total flow rate) and the gas flow rate for the purge passage (or the purge flow rate). As the control parameters, previously set default values may be used, or they may be appropriately modified or changed by an operator.

In the analysis mode, any one of the gas control modes among the constant linear velocity control mode, a constant column flow rate control mode, and a constant pressure control mode is used in accordance with the aim of the analysis or other purpose. In the gas chromatograph apparatus according to the present invention, regardless of the gas control mode selected during the analysis mode, any control mode of the gas control mode is changed to the constant pressure control mode in a transition to the waiting mode, and then fixed to the constant pressure control mode. In the constant pressure control mode, the gas feeding flow rate through the carrier gas passage, the gas ejection flow rate through the split passage, and other values are determined so that the column inlet pressure, i.e. the gas pressure in the sample vaporization chamber, is maintained at the target pressure. Therefore, even in the case where the viscosity of the carrier gas is extremely decreased and the resistance of the passage of the column becomes extremely small, the apparatus will not go out of control. However, if the target pressure is high, the column flow rate is increased and a carrier gas with a flow rate beyond the allowable upper limit might flow into the detector.

Given this factor, the flow rate determiner estimates, in advance of the transition to the waiting mode, the column flow rate corresponding to the lowest predicted value of the temperature in the column (such as the room temperature) after the transition to the waiting mode by using the control parameters memorized in the memory. Then, the flow rate determiner compares the estimated value with a previously set threshold value. In the case where the estimated value of the flow rate exceeds the threshold value, i.e. in the case where the detector might be damaged, the pressure changer indicates, for example, a warning that the column inlet pressure should be decreased from the level at that point in time. Seeing this warning, the operator performs an operation to decrease the column inlet pressure and retries the transition to the waiting mode. This operation decreases the target pressure in the constant pressure control mode and thereby causes a corresponding decrease in the column flow rate. In this manner, the column flow rate can be eventually suppressed to a level lower than the allowable upper limit, which can prevent the detector in the waiting mode from being damaged. The pressure changer may automatically, without waiting for the user operation, decrease the column inlet pressure and recalculate the column flow rate after the transition to the waiting mode under the decreased column inlet pressure.

In an aspect of the gas chromatograph apparatus according to the present invention, the controller controls the flow controller in such a manner as to change the split flow rate (or the split ratio) as the temperature in the column oven decreases, after setting a carrier gas flow rate and a purge flow rate which are included in the control parameters memorized in the memory and then starting the control of the constant pressure control mode.

The passage resistance of the column decreases as the temperature in the column oven decreases. By increasing the split flow rate along with this change, the gas pressure in the sample vaporization chamber can be maintained constant while the carrier gas flow rate and the purge flow rate are each maintained at a predetermined value.

In the gas chromatograph apparatus according to the present invention, in the case where the column oven includes a heater and an air fan, it is preferable that the controller decreases, in a transition to the waiting mode, the temperature in the column oven to a predetermined temperature, halts the power supply to the heater, and then stops the air fan after a predetermined period of time has elapsed.

By making the air fan operate for a while even after the power supply to the heater is stopped, the heat stored in the heater is sufficiently released. This operation prevents the temperature in the column oven from increasing due to the afterheat of the heater after the air fan is stopped, thereby avoiding damage to the column by an unintended increase of temperature.

The gas chromatograph apparatus according to the present invention may include a resumption information memory unit for memorizing, when a change from the analysis mode to the waiting mode is commanded, status information which represents the status of each unit of the apparatus at that point in time as well as the control parameters, and the controller may read out, in a transition from the waiting mode to the analysis mode, the status information and the control parameters memorized in the resumption information memory unit and control each unit in such a manner as to resume the state which the apparatus was in before the transition to the waiting mode.

With this configuration, when making the transition to the analysis mode after a completion of the waiting mode, the apparatus promptly resumes the state which the apparatus was in before the transition to the waiting mode, without any troublesome operation by an operator. Therefore, an analysis can be started within a short waiting time.

With the gas chromatograph apparatus according to the present invention, even in the case where a detector with a low allowable upper limit of flow rate, such as a mass spectrometer, is used, the column flow rate in the waiting mode in which the power supply to the column oven is stopped can be assuredly suppressed to a level where the detector will not be damaged. Hence, the usage of a carrier gas and the power consumption can be sufficiently suppressed without causing damage to the apparatus.

In addition, since the transition from the analysis mode to the waiting mode is performed using control parameters previously memorized in the memory, an operator does not have to perform the troublesome task of creating a method including control parameters, taking into account a variety of conditions for the waiting mode.

BRIEF DESCRIPTION OF THE DRAWINGS

FIG. 2 is a flowchart of a transition operation from a normal ready-for analysis status to an energy-saving mode in the GC/MS of the present embodiment.

FIG. 3 is a flowchart of a resumption operation from the energy-saving mode to the normal ready-for-analysis status in the GC/MS of the present embodiment.

EXPLANATION OF THE NUMERALS

Figure 1:
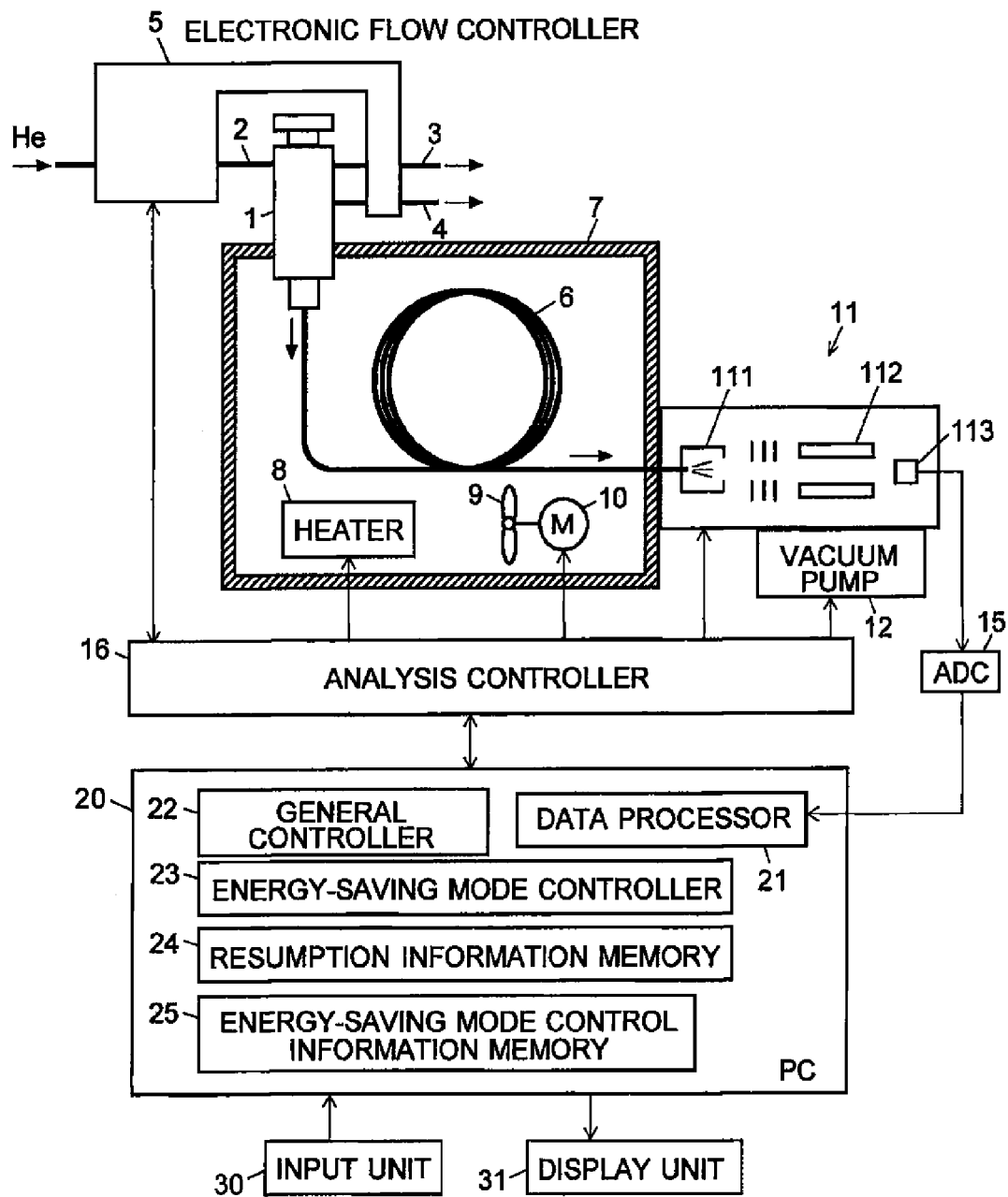
FIG. 1 is an entire configuration diagram of a GC/MS of an embodiment of the present invention.

1 . . . Sample Vaporization Chamber
2 . . . Carrier Gas Passage
3 . . . Purge Passage
4 . . . Split Passage
5 . . . Electronic Flow Controller
6 . . . Column
7 . . . Column Oven
8 . . . Heater
9 . . . Fan
10 . . . Motor
11 . . . Mass Analyzer
111 . . . Ionization Unit
112 . . . Mass Separation Unit
113 . . . Ion Detector
12 . . . Vacuum Pump
15 . . . A/D Converter (ADC)
16 . . . Analysis Controller
20 . . . Personal Computer (PC)
21 . . . Data Processor
22 . . . General Controller
23 . . . Energy-Saving Mode Controller
24 . . . Resumption Information Memory
25 . . . Energy-Saving Mode Control Information Memory
30 . . . Input Unit
31 . . . Display Unit

DETAILED DESCRIPTION OF A PREFERRED EMBODIMENT

Hereinafter, a GC/MS, which is an embodiment of the gas chromatograph apparatus according to the present invention, will be described with reference to the attached figures. FIG. 1 is an entire configuration diagram of the GC/MS according to the present embodiment.

A column 6 which is a capillary column is placed in a column oven 7, and a sample vaporization chamber 1 is provided at the inlet of the column 6. A carrier gas passage 2, a purge passage 3, and a split passage 4 are connected to the sample vaporization chamber 1. A carrier gas, such as helium gas, is provided to the sample vaporizing chamber 1 via the carrier gas passage 2 by an electronic flow controller 5 which includes a pressure sensor, a valve, and other components. This carrier gas is further sent to the column 6. Unwanted gas discharged from a septum attached on the head of the sample vaporization chamber 1 is exhausted through the purge passage 3 to the outside. When a split analysis is performed, a portion of the carrier gas provided to the sample vaporization chamber 1 is exhausted to the outside through the split passage 4.

A heater 8 and a fan 9 which is driven by a motor 10 are placed in the column oven 7, and by operating them, the air in the column oven 7 is maintained at a constant temperature (in the case of a constant-temperature analysis) or temperature controlled in accordance with a predetermined temperature program (in the case of a temperature-programmed analysis). When a small amount of liquid sample is injected into the sample vaporization chamber 1 from an injector (not shown) at a predetermined timing while a carrier gas is provided to the column 6 at a substantially constant flow rate through the sample vaporization chamber 1, the liquid sample is vaporized in a short period of time and introduced into the column 6 by the flow of the carrier gas. While passing through the column 6, a variety of compounds included in the sample are separated, and then flow out from the column 6 at different time delays.

A mass analyzer 11 as a detector is connected to the outlet of the column 6. The molecules (or atoms) of the compounds injected into the mass analyzer 11 are ionized in an ionization unit 111, are separated in accordance with their mass-to-charge ratio (m/z) in a mass separation unit 112, and are detected by an ion detector 113. The inside of the chamber equipped with the ionization unit 111, mass separation unit 112, ion detector 113, and other units is maintained at a vacuum atmosphere by a vacuum pump 12. The detection signal produced by the ion detector 113 is converted to digital data by an A/D converter (ADC) 15 and sent to a data processor 21, which is a function block realized by a personal computer (PC) 20. The data processor 21 creates a chromatogram (e.g. total ion chromatogram or mass chromatogram) based on the detection data sequentially obtained as time progresses, and further performs a qualitative or quantitative analysis by performing a predetermined waveform processing.

Under the direction of a general controller 22 which is a function block realized by the PC 20, the analysis controller 16 controls the electronic flow controller 5, the heater 8, the motor 10, components of the mass analyzer 11, and other units to accomplish an intended analysis operation of GC/MS. An input unit 30 for allowing a user (or analyst) to provide a variety of commands and set conditions and a display unit 31 for displaying analysis results and other information are connected to the PC 20. To perform a characteristic control as will be described later, the GC/MS of the present embodiment includes an energy-saving mode controller 23, a resumption information memory 24 and an energy-saving mode control information memory 25, which are function blocks realized by the PC 20.

Next, a detailed explanation will be made for a transition operation from a normal ready-for-analysis status (which corresponds to the "analysis mode" of the present invention) to an energy-saving mode (which corresponds to the "waiting mode" of the present invention) and a resumption operation from the energy-saving mode to the normal ready-for-analysis status, both of which are performed predominantly by the energy-saving mode controller 23 in the GC/MS of the present embodiment. FIG. 2 is a flowchart of a transition operation from the normal ready-for-analysis status to the energy-saving mode.

Control parameters for each unit in the energy-saving mode are memorized in the energy-saving mode control information memory 25. The control parameters include: a total flow rate, which is a gas feeding flow rate through the carrier gas passage 2; a purge flow rate, which is a gas ejection flow rate through the purge passage 3; a split ratio; the size of the column 6 (the length, internal diameter, film thickness of the liquid phase, and other values); and the temperature of the column oven. The control parameters also include the allowable upper limit of flow rate, which is the maximum allowable value of the column flow rate, and other values. This allowable upper limit of flow rate is generally determined by the configuration of the apparatus. For a GC/MS, since the gas flow rate which can be fed to a mass analyzer is low, the allowable upper limit of flow rate is generally determined by the configuration of the mass analyzer (e.g. evacuation capacity of the vacuum pump 12). As for the total flow rate and the purge flow rate, the minimum required flow rate is set as their default value.

When a command for executing the energy-saving mode is provided to the energy-saving mode controller 23 in response to a predetermined operation performed by an operator using the input unit 30 or by automatically following a predetermined sequence (Step S1), the energy-saving mode controller 23 obtains the latest status of the apparatus at that point in time and the variety of control parameters which have been set. Then, the energy-saving mode controller 23 stores these values as the resumption information in the resumption information memory 24 (Step S2).

Next, the energy-saving mode controller 23 computes the column flow rate Q during an execution of the energy-saving mode by using the status information obtained in Step S2 and the control parameters memorized in the energy-saving mode control information memory 25 (Step S3). For example, the status information used at this point in time may be the column inlet pressure and other values, and the control parameters used at the same time may be the temperature of the column oven, the size of the column 6, and other values. The column flow rate Q computed in Step S3 represents a column flow rate that is expected in the case where the energy-saving mode is executed under the conditions set at that point in time.

Subsequently, the column flow rate Q obtained by the computation in Step S3 and the allowable upper limit of flow rate P memorized in the energy-saving mode control information memory 25 are compared to determine whether Q is not higher than P (Step S4). If the column flow rate Q is higher than the allowable upper limit of flow rate P and the energy-saving mode is executed under this condition, an excessive amount of carrier gas might flow into the ionization unit 111 of the mass analyzer 11 to cause damage to the apparatus. To avoid this, in the case where the determination result in Step S4 is "No," the energy-saving mode controller 23 indicates a warning on the screen of the display unit 31 that urges users to decrease the column inlet pressure at that point in time and once again perform the command for executing the energy-saving mode (Step S11). If this warning is shown, the operator appropriately decreases the column inlet pressure (or the gas pressure in the sample vaporization chamber 1) and then enters the command for executing the energy-saving mode (Step S12). This returns the operation to Step S1.

On the other hand, in the case where the determination result in Step S4 was "Yes," the energy-saving mode controller 23 changes the gas control mode to the constant pressure control mode even in the case where the gas control mode of the sample vaporization chamber 1 at that point in time is in the constant linear velocity control mode or in the constant column flow rate control mode. Then, the energy-saving mode controller 23 sets the gas pressure in the sample vaporization chamber 1 as the target pressure to be maintained constant, and starts the constant pressure control (Step S5). With the target pressure thus set, the energy-saving mode controller 23 commands the electronic flow controller 5 via the analysis controller 16 to perform a control aimed at the setting values of the total flow rate and the purge flow rate memorized in the energy-saving mode control information memory 25 (Step S6). Consequently, the gas pressure in the sample vaporization unit 1 is maintained substantially constant.

Next, when the temperature of the column oven corresponding to the energy-saving mode is at the room temperature, the energy-saving mode controller 23 decreases, through the analysis controller 16, the temperature in the column oven 7 to a predetermined temperature and then turns off the heater 8 (Step S7). The predetermined temperature set in this operation is a temperature at which the column 6 will not be damaged, e.g. 50° C. Then, the energy-saving mode controller 23 waits until a predetermined time has passed (e.g. for 15 seconds) since that point in time (Step S8), halts the driving of the motor 10 to stop the fan 9 (Step S9), and further turns off an ion gauge (not shown) for detecting the degree of vacuum in the chamber of the mass analyzer 11 (Step S10).

The ion gauge may be turned off simultaneously with the stoppage of the fan 9. Although it is necessary to maintain the inside of the chamber of the mass analyzer 11 at a vacuum atmosphere, the degree of vacuum can be lower than that for the analysis. Hence, the number of revolutions of the vacuum pump (turbo molecular pump) 12 may be decreased simultaneously with the stoppage of the fan 9 in order to decrease the power consumption in the pump 12.

In any case, the transition to the energy-saving mode is completed with the previously described series of operations. When the PC 20 is used exclusively for this GC/MS, the PC 20 itself may shift to the energy-saving mode after each unit of the GC/MS has shifted to the energy-saving mode. In particular, the PC 20 may shift to the stand-by status or only the display may go to the save mode.

As described previously, before the transition to the energy-saving mode, whether or not the column flow rate exceeds the allowable upper limit of flow rate in the state of the energy-saving mode is checked, and the mode of controlling carrier gas is changed to the constant pressure control mode. As the viscosity of the carrier gas decreases according to a gradual decrease in the temperature of the column, the column flow rate gradually increases. Since the total flow rate and the purge flow rate are maintained constant, the increase of the column flow rate is covered by a gradual decrease in the split flow rate. Although the column flow rate increases, it will not exceed the allowable upper limit of flow rate even with the temperature of the column oven as low as the room temperature. This prevents the mass analyzer 11 from being damaged.

Since the fan 9 is turned off with a delay after the heater 8 of the column oven 7 is turned off, it is possible to prevent the temperature in the column oven 7 from increasing again due to the afterheat of the heater 8. This allows a reduction of the power consumption during a standby period for analysis, while preventing heat damage to the column 6.

FIG. 3 is a flowchart of a resuming operation from the energy-saving mode to the normal ready-for-analysis status. For example, when an operator performs a predetermined operation with the input unit 30 in order to initiate an analysis, a command for canceling the energy-saving mode is given to the energy-saving mode controller 23 (Step S21). The energy-saving mode controller 23 reads out the status of the apparatus and the control parameters which were obtained at the moment immediately before the transition to the energy-saving mode and previously memorized in the resumption information memory 24, and then provides them to the general controller 22 (Step S22).

The general controller 22 starts to control each unit of the GC/MS in accordance with the read status of the apparatus and the control parameters (Step S23). For example, the general controller 22 starts the power supply to the heater 8 in order to return the temperature of the column oven 7 to the former temperature and simultaneously starts the power supply to the motor 10 to operate the fan 9. In the case where the gas control mode before the transition to the energy-saving mode was the constant flow rate control mode or the constant liner velocity control mode, the constant pressure control mode is terminated and the gas control mode returns to the former gas control mode. Accordingly, the apparatus promptly resumes the state which it was in before the transition to the energy-saving mode (Step S24), allowing an analysis to be performed from that state.

In the aforementioned embodiment, a warning that the column inlet pressure should be decreased is displayed in Step S11 and the operator performs an operation to decrease the column inlet pressure. However, the column inlet pressure may be automatically decreased by a predetermined amount and the process may return to Step S1. This is advantageous in that the operator does not have to perform the task of changing the setting value of the column inlet pressure each time. Nonetheless, even in this case, it is preferable to display a notice that the column inlet pressure has been automatically decreased.

In the aforementioned embodiment, only one column is connected to the ionization unit 111 of the mass analyzer 11. In a GC/MS described in Japanese Unexamined Patent Application Publication No. 2006-162515, the downstream ends of a plurality of columns provided parallel to each other are connected to the ionization unit. In such a configuration, a carrier gas flows into the ionization unit from each of the plurality of columns. Hence, it is necessary to prevent the total amount of the gas flow from exceeding the allowable upper limit value determined by the configuration of the mass analyzer. Given this factor, in such a case, the sum of the column flow rates of the plurality of columns may be compared with the allowable upper limit of the flow rate to determine whether or not the parameters set for the energy-saving mode are appropriate.

It should be noted that the embodiments described thus far are merely an example of the present invention, and it is evident that any modification, adjustment, or addition made within the spirit of the present invention is also included in the scope of the claims of the present application.

What is claimed is:

1. A gas chromatograph apparatus having at least two switchable operation modes, one mode being an analysis mode in which an analysis of a sample can be performed and another mode being a waiting mode in which no analysis is performed, where the gas chromatograph apparatus includes: a column placed in a column oven; a sample vaporization chamber provided at an inlet of the column; a carrier gas passage for feeding a carrier gas to the sample vaporization chamber; a purge passage for ejecting an impurity gas from the sample vaporization chamber; a split passage for ejecting a portion of the carrier gas from the sample vaporization chamber; a flow controller for interlockingly controlling flow rates of gases flowing through the carrier gas passage, the purge gas passage and the split passage as well as a gas pressure in the sample vaporization chamber, the flow controller having a constant linear velocity control mode, a constant column flow rate control mode, and a constant pressure control mode, as a gas control mode; and a detector for detecting a sample component in a gas which has passed through the column,
wherein the gas chromatograph apparatus further includes:
 a) a memory for memorizing control parameters for the waiting mode, the control parameters including a minimum value of a gas flow rate required for each of the carrier gas passage and the purge passage in the waiting mode; and
 b) a controller for setting, in a transition from the analysis mode to the waiting mode, the gas control mode to the constant pressure control mode regardless of the gas control mode in the analysis mode, for setting a column inlet pressure at that point in time as a target pressure, and for controlling the flow controller using the control parameters memorized in the memory,
and the controller includes:
 a flow rate determiner for estimating, in advance of the transition to the waiting mode, a column flow rate corresponding to a lowest predicted value of a temperature in the column after the transition to the waiting mode by using the control parameters memorized in the memory, and for comparing the estimated value with a preset threshold value; and
 a pressure changer for providing a warning to a user that the column inlet pressure at that point in time should be decreased or automatically decreasing the column inlet pressure in a case where the estimated value of the flow rate exceeds the threshold value.

2. The gas chromatograph apparatus according to claim 1, wherein:
the controller controls the flow controller in such a manner as to change a split flow rate as the temperature in the column oven decreases, after setting a carrier gas flow rate and a purge flow rate which are included in the control parameters memorized in the memory and starting a control of the constant pressure control mode.

3. The gas chromatograph apparatus according to claim 2, wherein:
the column oven includes a heater and an air fan; and
the controller decreases, in a transition to the waiting mode, a temperature in the column oven to a predetermined temperature, halts a power supply to the heater, and then stops the air fan after a predetermined period of time has elapsed.

4. The gas chromatograph apparatus according to claim 3, comprising a resumption information memory unit for memorizing, when a change from the analysis mode to the waiting mode is commanded, status information which represents a status of each unit of the apparatus at that point in time as well as the control parameters, wherein the controller reads out, in a transition from the waiting mode to the analysis mode, the status information and the control parameters memorized in the resumption information memory unit and controls each unit in such a manner as to resume the state which the apparatus was in before the transition to the waiting mode.

5. The gas chromatograph apparatus according to claim 2, comprising a resumption information memory unit for memorizing, when a change from the analysis mode to the waiting mode is commanded, status information which represents a status of each unit of the apparatus at that point in time as well as the control parameters, wherein the controller reads out, in a transition from the waiting mode to the analysis mode, the status information and the control parameters memorized in the resumption information memory unit and controls each unit in such a manner as to resume the state which the apparatus was in before the transition to the waiting mode.

6. The gas chromatograph apparatus according to claim 1, wherein:
the column oven includes a heater and an air fan; and
the controller decreases, in a transition to the waiting mode, a temperature in the column oven to a predetermined temperature, halts a power supply to the heater, and then stops the air fan after a predetermined period of time has elapsed.

7. The gas chromatograph apparatus according to claim 6, comprising a resumption information memory unit for memorizing, when a change from the analysis mode to the waiting mode is commanded, status information which represents a status of each unit of the apparatus at that point in time as well as the control parameters, wherein the controller reads out, in a transition from the waiting mode to the analysis mode, the status information and the control parameters memorized in the resumption information memory unit and controls each unit in such a manner as to resume the state which the apparatus was in before the transition to the waiting mode.

8. The gas chromatograph apparatus according to claim 1, comprising a resumption information memory unit for memorizing, when a change from the analysis mode to the waiting mode is commanded, status information which represents a status of each unit of the apparatus at that point in time as well as the control parameters, wherein the controller reads out, in a transition from the waiting mode to the analysis mode, the status information and the control parameters memorized in the resumption information memory unit and controls each unit in such a manner as to resume the state which the apparatus was in before the transition to the waiting mode.

* * * * *